US011378562B2

(12) United States Patent
Rubeinstein et al.

(10) Patent No.: US 11,378,562 B2
(45) Date of Patent: Jul. 5, 2022

(54) SELF-TIMING MODULE PASSIVE CHEMICAL DOSIMETERS

(71) Applicant: Government of the United States as represented by the Secretary of the Air Force, Wright-Patterson AFB, OH (US)

(72) Inventors: H Mitchell Rubeinstein, Beavercreek, OH (US); Christin M Duran, Dayton, OH (US); Daniel O Reilly, Kettering, OH (US); Steven D Fisher, Dayton, OH (US); Anthony V Qualley, Washington Township, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 236 days.

(21) Appl. No.: 16/884,711

(22) Filed: May 27, 2020

(65) Prior Publication Data

US 2021/0372982 A1    Dec. 2, 2021

(51) Int. Cl.
*G01N 33/00* (2006.01)
*G01N 31/22* (2006.01)
*G01N 1/22* (2006.01)

(52) U.S. Cl.
CPC ....... *G01N 33/0062* (2013.01); *G01N 31/224* (2013.01); *G01N 33/0047* (2013.01); *G01N 2001/2276* (2013.01); *Y10S 436/902* (2013.01)

(58) Field of Classification Search
CPC ............... G01N 31/223; G01N 31/224; G01N 33/0062; G01N 1/2273; G01N 2001/2276

(Continued)

(56) References Cited

U.S. PATENT DOCUMENTS 5,145,645 A * 9/1992 Zakin ................... G01N 27/126
                                                      422/90
2020/0393341 A1* 12/2020 Smith .................. G01N 1/2247

FOREIGN PATENT DOCUMENTS

WO    WO-2011100061 A2 *  8/2011    ........... G01N 1/2214
WO    WO-2020240600 A1 * 12/2020    ........... G01N 1/2214

OTHER PUBLICATIONS

EPA, "Passive Samplers for Investigators of Air Quality: Method description, implementation, and comparison to alternative sampling methods," Engineering Issue, Dec. 2004, 44 pages total.

(Continued)

*Primary Examiner* — Nathaniel J Kolb
(74) *Attorney, Agent, or Firm* — AFMCLO/JAZ; Chastity D. S. Whitaker

(57) ABSTRACT

A self-timing, passive, chemical dosimeter. The dosimeter includes a sampling media and electronics supported by a cassette. The sampling media is configured to absorb volatile organic compounds, semivolatile organic compounds, or both, while the electronics are configured to record a time of exposure. The dosimeter further includes an actuator having a closed position and an open position. In the closed position, the actuator resists exposure of the sampling media to volatile organic compounds, semivolatile organic compounds, or both, and in the open position, the actuator permits exposure of the sampling media to volatile organic compounds, semivolatile organic compounds, or both. The actuator is configured to operate the electronics for recording time of exposure.

15 Claims, 3 Drawing Sheets

(58) Field of Classification Search
USPC .......................................................... 436/902
See application file for complete search history.

(56) References Cited

OTHER PUBLICATIONS

SKC Inc., "Passive Diffusive Samplers: A Comprehensive Review," available at https://www.skcinc.com/catalog/presentations/Features/archives/Passive_Samplers_Comprehensive_Review_2017.pdf, 2017, 61 pages total.

* cited by examiner

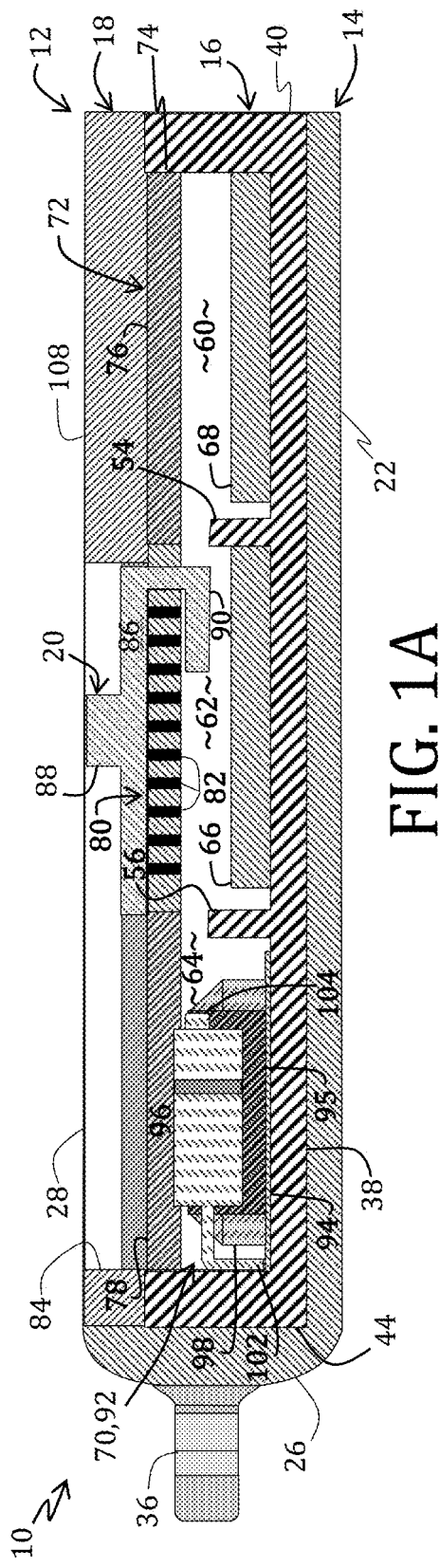

SELF-TIMING MODULE PASSIVE CHEMICAL DOSIMETERS

RIGHTS OF THE GOVERNMENT

The invention described herein may be manufactured and used by or for the Government of the United States for all governmental purposes without the payment of any royalty.

FIELD OF THE INVENTION

The present invention relates generally to dosimeters and, more particularly, to automated dosimeters.

BACKGROUND OF THE INVENTION

Volatile- and semivolatile organic compounds (VOC and SVOC, respectively) are classes of compounds that have high vapor pressure at room temperature resulting from a low boiling point. While many naturally occurring VOCs are harmless (such as scents or pheromones), others are acutely toxic and/or have respiratory, allergic, or immune effects on organisms. These harmful VOCs and SVOCs include, for example, benzene, dichlorobenzene, ethanol, formaldehyde, terpenes, toluene, xylene, polybrominated flame-retardants, phthalates, pesticides, and polycyclic aromatic hydrocarbons. Still more dangerous VOCs and SVOCs may include agents used in chemical warfare.

Personal dosimeters are devices worn by individuals such that their exposure to harmful agents may be identified, quantified, or both. Dosimeters operate according to Fick's Law, where a sample amount, Q, adsorbed onto a sampling media may be expressed as a function of a compound specific diffusion coefficient, D, and a geometric constant of the dosimeter, K:

$$Q = D*K$$

Because the diffusion coefficient remains constant, improvements to a measured sampling rate requires manipulating the geometric constant, K. This geometric constant is a function of a cross-sectional area of a diffusion path, A, diffusion path length, L, an airborne concentration, C, and a sampling time, T:

$$K = \left(\frac{A}{L}\right)*CT.$$

Therefore, personal dosimeters conventionally include a tube, badge, or other similar style that is worn during the possible exposure. For accurate analysis, the exposure time, both date and time, must be specifically recorded. While this may be an inconvenience to individuals within a laboratory setting, it can be difficult to impossible to individuals working in the field.

Besides timekeeping, conventional, passive dosimeters present other difficulties. Those devices utilizing a power source require battery replacement or recharging. Manipulating small batteries and components is not feasible in the field, particularly in the field of battle, when a soldier may be carrying a large weight of gear.

In view of these conventional devices, there remains a need for a passive dosimeter that self-reports exposure times, is replaceable, and configured in a manner that facilitates quick and ease of use.

SUMMARY OF THE INVENTION

The present invention overcomes the foregoing problems and other shortcomings, drawbacks, and challenges of conventional, passive dosimeters. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention a self-timing, passive, chemical dosimeter includes a sampling media and electronics supported by a cassette. The sampling media is configured to absorb volatile organic compounds, semivolatile organic compounds, or both, while the electronics are configured to record a time of exposure. The dosimeter further includes an actuator having a closed position and an open position. In the closed position, the actuator resists exposure of the sampling media to volatile organic compounds, semivolatile organic compounds, or both, and in the open position, the actuator permits exposure of the sampling media to volatile organic compounds, semivolatile organic compounds, or both. The actuator is configured to operate the electronics for recording time of exposure.

Other embodiments of the present invention are directed to a method of measuring exposure to volatile organic compounds, semivolatile organic compounds, or both using a dosimeter. The method includes moving an actuator of the dosimeter from a closed position to an open position. Movement of the actuator to the open position exposes a sampling media, which is configured to absorb volatile organic compounds, semivolatile organic compounds, or both if present. Movement of the actuator to the closed position resists exposing the sample media. Movement of the actuator is also configured to activate electronics that are configured to record a date and a time of the movement.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIG. 1A is a cross-sectional view of the passive dosimeter of FIG. 1 taken along the line 1A-1A.

FIG. 3A is a cross-sectional view of the passive dosimeter of FIG. 3 taken along the line 3A-3A.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 1:
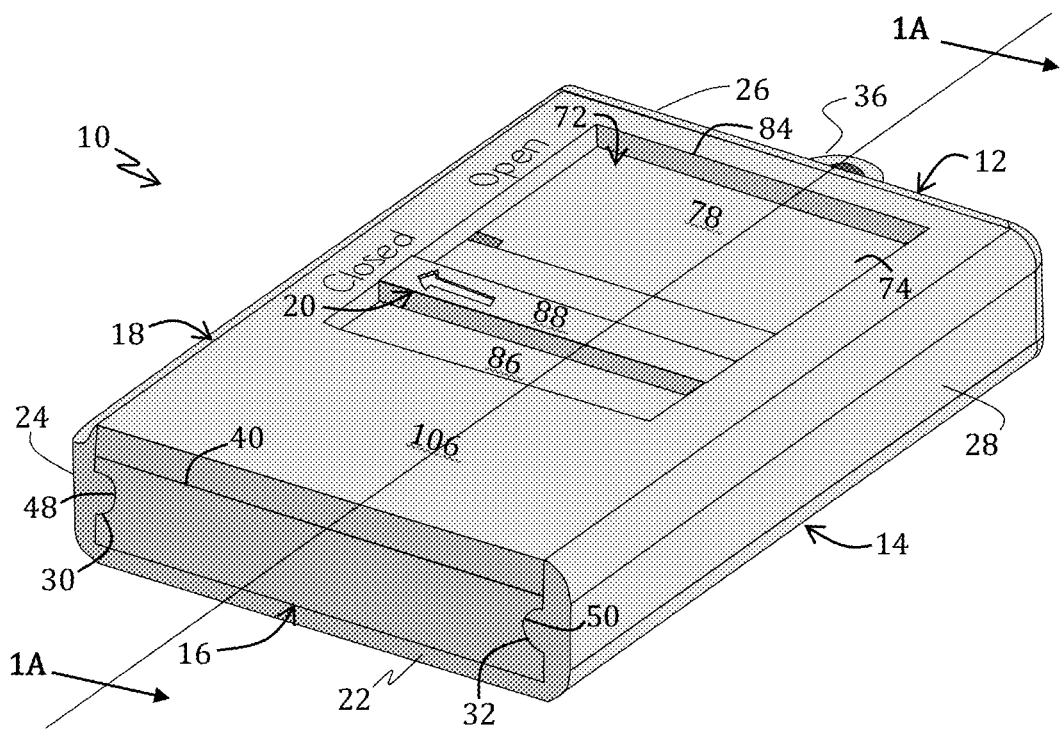
FIG. 1 is an orthographic view of a passive dosimeter according to an embodiment of the present invention.
Figure 2:
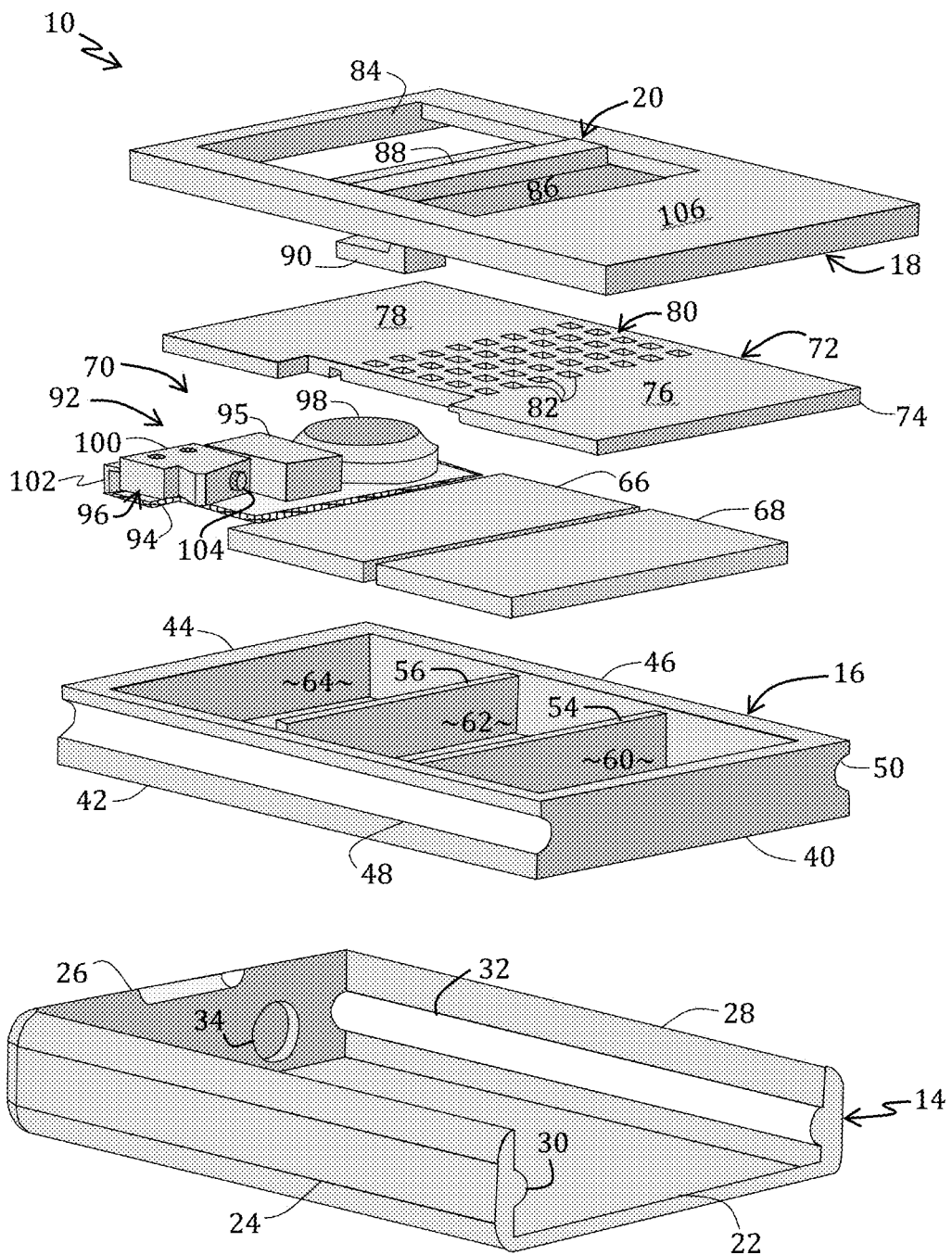
FIG. 2 is an exploded, orthographic view, of the passive dosimeter of FIG. 1.

Referring now to the figures, and in particular to FIGS. 1, 1A, and 2, a passive dosimeter 10 according to an embodiment of the present invention is described. The passive dosimeter 10 includes a casing 12 comprising a holster 14 configured to receive a cassette 16 and a cover 18 with a slidable shutter 20. The slidable shutter 20 is configured to be an actuator that activates timing electronics for recording exposure time. While various shapes and sizes are possible, the particular illustrative embodiment provides a rectangularly shaped holster 14 having and a base floor 22 and three walls 24, 26, 28 extending orthogonally from the base floor 22. While not required, each of two of the illustrated three walls 24, 28, i.e., the opposing walls, includes a rail 30, 32 for slidably engaging the cassette 16. The third wall 26 may include an indentation 34, or other similar structure, to facilitate proper alignment and complete placement of the cassette 16 with respect to the holster 14.

According to some embodiments, the holster 14 may be configured in a manner that is similar to a badge holder. That is, the holster 14 may include a hook 36 for receiving an alligator clip (not shown), lanyard (not shown), or other like structure that would be configured to secure a badge to the user. Moreover, the holster 14 may be constructed from a variety of materials according to the intended use, but generally includes polymers, metals, and so forth that may be molded, extruded, or produced by additive manufacturing processes, for example.

The cassette 16, as is shown in the embodiment of FIG. 2, is rectangularly shaped, similar to the holster 14, but sized so as to be received by the holster 14. This particular embodiment of the cassette 16 includes a base 38 and four walls 40, 42, 44, 46 extending orthogonally away from the base 38. Each of two opposing 42, 46 walls may include a recess 48, 50 that is configured to receive the rails 30, 32 of the walls 24, 28 of the holster 14 so that the cassette 16 may slide along the rails 30, 32 by way of the recesses 48, 50.

The four walls 40, 42, 44, 46 of the cassette 16 define an interior volume that may, optionally, be separated by one or more walls (two walls 54, 56 are shown) into a plurality of compartments (three compartments 60, 62, 64). The compartments 60, 62, 64 may be numbered, sized, and shaped to receive or accommodate a sampling media 66, optionally a blank media 68, electronics 70, and other accessories as would be desired or necessary according to various embodiments.

The cassette 16 may be constructed in a manner similar to the holster 14, using materials and methods described above.

The cassette 16 is configured to receive a screen 72, which may be a sheet 74 of material (such as those described above with respect to the holster) having a solid portion (two solid portions 76, 78 are shown) and a filter portion 80. The solid portions 76, 78 are configured to cover those compartments 60, 64 of the cassette 16 that are not intended to be exposed; the filter portion 80, which is illustrated as a plurality of orifices 82 extending through the sheet 74, is configured to cover the compartment 62 of the 16 cassette that is intended to be exposed.

Figure 3:
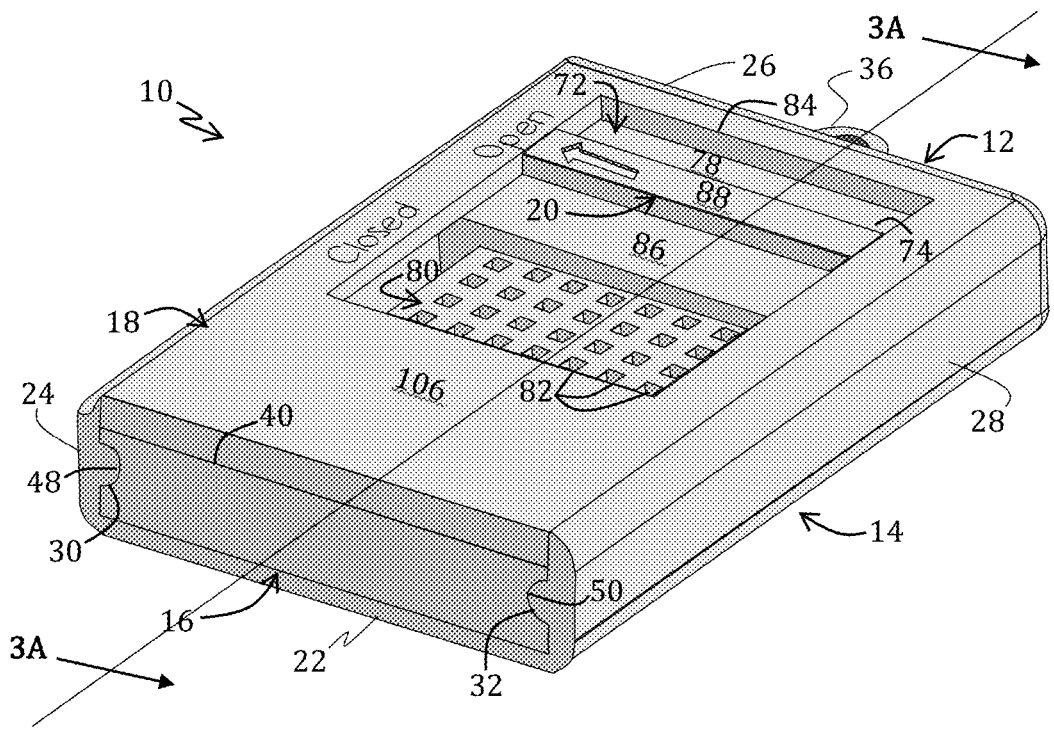
FIG. 3 is orthographic view of the passive dosimeter of FIG. 1 configured for exposure to harmful agents.

The cover 18, which may reside above the screen 72, is received by the holster 14, encloses the cassette 16 and screen 72 within the holster 14, and includes a window 84 that may be closed by the slidable shutter 20. A position of the cover 18 may be retained by friction fit, magnets, epoxy, or other methods that are known to those of ordinary skill in the art having the benefit of the disclosure made herein. As with the holster 14, the cassette 16, and the screen 72, the cover 18 may be constructed from materials and according to methods that are similar to those described for these other elements. The slidable shutter 20 may include a surface 86 that is configured to cover at least the filter portion 80 of the screen 72, a user tab 88 extending outwardly from the sheet 74 and the holster 14, and an activating tab 90 extending inwardly from the sheet 74 and into the holster 14 and the cassette 16. The surface 86 of the slidable shutter 20 should cover the filter portion 80 of the screen 72 while leaving the solid portion 76 of the screen 72 exposed through the window 84 (FIG. 1) or cover the solid portion 76 of the screen 72 while leaving the filter portion 80 of the screen 72 exposed through the window 84 (FIG. 3).

Referring specifically now to FIG. 2, the compartments 60, 62, 64 of the cassette 16 are configured to receive the blank media 68, the sampling media 66, and the electronics 70, respectively.

The sampling media 66 may comprise any suitable material known to absorb the VOC or SVOC of interest. Exemplary materials, particularly useful for VOC and SVOCs, may include carbon, zeolite, polymers, or other proprietary blends that are known by those of ordinary skill in the art. The sampling media 66 may be sized and shaped so as to be received by the selected compartment 62 of the cassette 16 in proximity to the filter portion 80 of the screen 72.

If the blank media 68 is included (as in the in the particular, illustrated embodiment), the blank media 68 is configured to be a negative control for the dosimeter 10. In that way, the blank media 68 may be constructed in a manner similar to the sampling media 66 and received by the selected compartment 60 of the cassette 16 in proximity to the solid portion 76 of the screen 72.

The electronics 70 may vary according to particular embodiments and desired application, such as whether the dosimeter 10 is configured to be turned off/on, whether date and time records are to be maintained, whether a rate of exposure is to be measured, and so forth. For the particular embodiment of FIG. 2, the electronics 70 include a conventional printed circuit board ("PCB") timer 92 having a circuit board 94 configured to control and operate other components, a processor 95 configured to capture data related to activation and deactivation (such as time and date), a switch 96 operably coupled to the slidable shutter 20 and a power source 98. The switch 96 of the illustrated embodiment is a sub-mini snap action switch; however, those of ordinary skill in the art having the benefit of the disclosure made herein may use other switches. The action switch 96 include a housing 100, an NC terminal (not shown), an NO terminal), a common terminal 102, and an actuating button 104. The actuating button 104 is positioned so as to be aligned with the activating tab 90 of the slidable shutter 20.

In use, and with reference now to FIGS. 1, 1A, 3, and 3A, when a user is not being exposed (or not in an environment of potential exposure) to VOCs or SVOCs, the slidable shutter 20 may be positioned in a closed configuration (FIGS. 1 and 1A) such that the surface 86 of the slidable shutter 20 covers the filter portion 80 of the screen 72 to leave the solid portion 78 of the screen 72 exposed through the window 84. In some embodiments, such as in FIG. 1, the cover 18 may include indicia ("Open," "Closed," and an arrow on the user tab) to facilitate use of the dosimeter 10. According to FIG. 1A, with the surface 86 of the shutter 20 in the closed position, the filter portion 80 of the screen 72 is covered and the activating tab 90 of the shutter 20 is aligned with, but spaced away from, the actuating button 104 of the action switch 96.

The user tab 88 is utilized to facilitate movement of the shutter 20 from the closed position of FIG. 1 to the open position of FIG. 3. Accordingly, the surface 86 now covers the solid portion 78 the screen 72 to leave the filter portion 80 of the screen 72 exposed through the window 84.

Furthermore, and according to FIG. 3A, with the surface 86 of the shutter 20 in this open position, the filter portion 80 of the screen 72 is exposed, and the activating tab 90 of the shutter 20 is aligned with and depressing the actuating button 104 of the action switch 96. With the actuating button 104 depressed, internal elements (not shown) of the action switch 96 are manipulated so as to complete the timer circuit, as powered by a watch battery 98 (i.e., the illustrated power source). Thereafter, when the user tab 88 is moved to the closed position, the activating tab 90 moves away from the actuating button 104 so that the latter is released from the depressed position, and the timer circuit is broken.

It would be readily appreciated that in FIGS. 1 and 3, the blank media 68, if present, remains covered by the solid portion 76 of the screen 72 as well as a solid portion 106 and the cover 18 to reduce a chance of exposure.

A particular advantage to the dosimeter 10 illustrated in FIGS. 1 and 3 is an ability to replace parts as necessary. For instance, the sampling media 66, the blank media 68, and electronics 70 (such as the power source 98) may be removed and replaced with fresh media 66, 68 or electronics 70 by sliding the cassette 16, screen 72, and cover 18 from the holster 14 and exposing the compartments 60, 62, 64 of the cassette 12. However, all components need not be replaced simultaneously as the useable lifespan of each component may vary.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A dosimeter comprising:
   a sampling media configured to absorb volatile organic compounds, semivolatile organic compounds, or both for quantification thereof;
   electronics configured to record a time of exposure;
   a cassette configured to support the sampling media and the electronics; and
   an actuator having a closed position that resists exposure of the sampling media to volatile organic compounds, semivolatile organic compounds, or both, and an open position that permits exposure of the sampling media to volatile organic compounds, semivolatile organic compounds, or both, and to operate the electronics to record the time of exposure.

2. The dosimeter of claim 1, wherein the sampling media is carbon, zeolite, polymers, or combinations thereof.

3. The dosimeter of claim 1, wherein the electronics include a timer.

4. The dosimeter of claim 3, wherein the timer is a printed circuit board timer.

5. The dosimeter of claim 3, wherein the timer is configured to record a date and a time associated with each movement of the actuator to the closed position and to the open position.

6. The dosimeter of claim 1, wherein the actuator comprises:
   a cover for the cassette, wherein the cover includes a window extending therethrough; and
   a shutter configured to slide in relation to the window to resist or permit exposure of the sampling media; and
   an activating tab operably coupled to the shutter and configured to activate the electronics.

7. The dosimeter of claim 1, further comprising:
   a holster configured to support the actuator, the cassette, and the electronics and sampling media within the cassette.

8. The dosimeter of claim 1, further comprising:
   a blank media configured to be a negative control with the sampling media.

9. The dosimeter of claim 1, further comprising:
   a holster configured to support the cassette;
   a cover for the cassette, wherein the cover includes a window extending therethrough; and
   a shutter configured to slide in relation to the window to resist or permit exposure of the sampling media; and
   an activating tab operably coupled to the shutter and configured to activate the electronics.

10. The dosimeter of claim 1, wherein the sampling media and the electronics are configured to be removable from the cassette.

11. The dosimeter of claim 10, wherein a replacement sampling media and replacement electronics are configured to be placed into the cassette.

12. A method of measuring exposure to volatile organic compounds, semivolatile organic compounds, or both using a dosimeter, the method comprising:
   moving an actuator of the dosimeter from a closed position to an open position, whereby when the actuator is in the open position a sampling media is exposed, the sampling media configured to absorb volatile organic compounds, semivolatile organic compounds, or both; and
   activating, by moving the actuator, electronics configured record a date and a time of the movement.

13. The method of claim 12, further comprising:
   quantifying an amount of volatile organic compound, an amount of semivolatile organic compound, or both absorbed onto the sampling media.

14. The method of claim 13, further comprising:
   correlating the amount of volatile organic compound, the amount of semivolatile organic compound, or both with a time of exposure recorded by the electronics.

15. The method of claim 13, wherein the dosimeter further comprises a blank media configured to be a negative control with the sampling media, the method further comprising:
   comparing the amount of volatile organic compound, the amount of semivolatile organic compound, or both of the sampling media with an amount of volatile organic compound, an amount of semivolatile organic compound, or both absorbed onto the blank media.

\* \* \* \* \*